United States Patent
Degeal et al.

(10) Patent No.: US 8,889,072 B2
(45) Date of Patent: Nov. 18, 2014

(54) FLOW CYTOMETER SORTER

(75) Inventors: Jeffrey W. Degeal, Loveland, CO (US); Charles S. Bay, Fort Collins, CO (US); Edward A. Stanton, Longmont, CO (US); Paul Barclay Purcell, Ouray, CO (US); George C. Malachowski, Melbourne (AU)

(73) Assignee: Beckman Coulter, Inc., Brea, CA (US)

( * ) Notice: Subject to any disclaimer, the term of this patent is extended or adjusted under 35 U.S.C. 154(b) by 46 days.

(21) Appl. No.: 13/615,076

(22) Filed: Sep. 13, 2012

(65) Prior Publication Data

US 2013/0244317 A1 Sep. 19, 2013

Related U.S. Application Data

(62) Division of application No. 12/098,340, filed on Apr. 4, 2008, now Pat. No. 8,290,625.

(60) Provisional application No. 60/917,854, filed on May 14, 2007, provisional application No. 60/910,646, filed on Apr. 7, 2007, provisional application No. 60/921,753, filed on Apr. 4, 2007.

(51) Int. Cl.

| | | |
|---|---|---|
| *G01N 21/00* | (2006.01) | |
| *G01N 21/05* | (2006.01) | |
| *G01N 33/48* | (2006.01) | |
| *G01N 35/08* | (2006.01) | |
| *G06F 17/00* | (2006.01) | |
| *C12Q 1/04* | (2006.01) | |
| *B07C 5/36* | (2006.01) | |
| *B07C 5/342* | (2006.01) | |

(52) U.S. Cl.
CPC *G06F 17/00* (2013.01); *C12Q 1/04* (2013.01); *B07C 5/361* (2013.01); *B07C 5/342* (2013.01)

USPC .......... 422/73; 422/67; 702/21; 702/26; 702/29; 700/266; 436/43; 436/52; 436/53

(58) Field of Classification Search
USPC .......... 436/43; 422/62–63, 68.1, 93, 509, 73; 700/266, 29; 702/21, 26
See application file for complete search history.

(56) References Cited

U.S. PATENT DOCUMENTS

| | | |
|---|---|---|
| 4,181,954 A | 1/1980 | Rosenthal et al. |
| 5,199,576 A | 4/1993 | Corio et al. |

(Continued)

OTHER PUBLICATIONS

Bond, C., "A New Algorithm for Scan Conversion of a General Ellipse," available online at http://www.crbond.com/papers/ellipse.pdf, Jan. 15, 2002, 11 pages, (las accessed Aug. 13, 2008).

(Continued)

*Primary Examiner* — Brian R Gordon
(74) *Attorney, Agent, or Firm* — K&L Gates LLP; Louis C. Cullman; Andrew L. Reibman

(57) ABSTRACT

Disclosed are computer-implemented methods of sorting particles from a particle stream in a flow cytometer. The methods include: calculating sort decision making parameters using the raw event data values from a flow cytometer and a sort logic; performing sort logic computations using the sort logic definition and the sort decision making parameters to generate sort decisions; converting the sort decisions into sort commands; and sending the one or more sort commands to the flow cytometer. Sort logic computations may include algorithmically using conditional branching logic, and may include sort logic equations having mathematical functions characterizing one or more regions of interest in multidimensional data space. Such mathematical functions may be determined based on one or more parameters provided by a user. Also disclosed are corresponding systems having a flow cytometer and a computer.

18 Claims, 11 Drawing Sheets

(56) References Cited

U.S. PATENT DOCUMENTS

| | | | |
|---|---|---|---|
| 5,548,661 | A | 8/1996 | Price et al. |
| 5,550,058 | A | 8/1996 | Corio et al. |
| 5,856,665 | A | 1/1999 | Price et al. |
| 5,983,211 | A | 11/1999 | Heseltine et al. |
| 5,998,212 | A | 12/1999 | Corio et al. |
| 7,043,500 | B2 | 5/2006 | Leary |
| 7,349,837 | B2 | 3/2008 | Martin et al. |
| 7,758,811 | B2 | 7/2010 | Durack et al. |
| 7,799,569 | B2 | 9/2010 | Durak et al. |
| 7,943,384 | B2 | 5/2011 | Durack et al. |
| 8,290,625 | B2 | 10/2012 | Degal |
| 2010/0232675 | A1 | 9/2010 | Ortyn et al. |

OTHER PUBLICATIONS

Hearn, D., and Baker, M.P., "Circle-Generating Algorithms," in Computer Graphics, C version, 2nd Ed., Horton, M, ed., Prentice Hall, Inc., Upper Saddle River, NJ, pp. 97-103 (1997).

Wikipedia, "Conic section," available online at http://en.wikipedia.org/w/index.php?title=Conic, 10 pages, (last accessed Mar. 22, 2007).

Wikipedia, "Ellipse," available online at http://en.wikipedia.org/w/index.php?title=Ellipse, 11 pages, (last accessed Mar. 22, 2007).

Wikipedia, "Ellipsoid," available online at http://en.wikipedia.org/w/index.php?title=Ellipsoid, 8 pages, (last accessed Mar. 22, 2007).

Wikipedia, "Hyperbola," available online at http://en.wikipedia.org/w/index.php?title=Hyperbola, 9 pages, (last accessed Mar. 22, 2007).

Wikipedia, "Hyperboloid," available online at http://en.wikipedia.org/w/index.php?title=Hyperboloid, 5 pages, (last accessed Mar. 22, 2007).

Wikipedia, "Parabola," available online at http://en.wikipedia.org/w/index.php?title=Parabola, 15 pages, (last accessed Mar. 22, 2007).

Wikipedia, "Spheroid," available online at http://en.wikipedia.org/w/index.php?title=Spheroid, 6 pages, (last accessed Mar. 22, 2007).

Wikipedia, "Paraboloid," available online at http://en.wikipedia.org/w/index.php?title=Paraboloid, 7 pages, (last accessed Mar. 22, 2007).

FLOW CYTOMETER SORTER

CROSS REFERENCE TO RELATED APPLICATIONS

This is a divisional application that claims priority pursuant to 35 U.S.C. §120 to U.S. patent application Ser. No. 12/098,340, filed Apr. 4, 2008, a US Non-Provisional Patent Application, now U.S. Pat. No. 8,290,625 issued on Oct. 16, 2012, which claims the benefit of U.S. Provisional Application No. 60/917,854, filed May 14, 2007, U.S. Provisional Application No. 60/910,646, filed Apr. 7, 2007, and U.S. Provisional Application No. 60/921,753, filed Apr. 4, 2007, each of which is hereby incorporated by reference in its entirety.

BACKGROUND OF THE INVENTION

The present invention relates generally to particle sorting and more specifically to software-based particle sorting for flow cytometry.

Flow cytometry is a technology that is used to analyze multiple physical characteristics of single particles, such as single cells in fluid suspension. The characteristics and properties of cells that can be measured using flow cytometry include the size, granularity, proteins and Deoxyribonucleic Acid (DNA), internal complexity, fluorescence intensity and other features of the cells. The fluorescence intensity is based on the fluorescence of target particles in the flow stream that have been labeled with a fluorescent dye. Detectors, such as photomultiplier tubes, are used to detect forward scatter, side scatter and fluorescence in various spectra to measure various properties of the cell. The characteristics and properties that are identified by flow cytometers can then be used to analyze, identify and/or sort cells.

A typical flow cytometer uses three main systems, i.e., a fluidic system, an optical system and an electronics system. The fluidic system transports particles in a fluid stream past laser beams for illumination. The optical system includes lasers that illuminate individual particles in the fluid stream, optical filters that filter the light and photomultiplier tubes that detect fluorescence and/or scatter. The electronics system processes the analog signal generated by the photomultiplier tubes or other detectors, processes those signals in analog and/or digital form, provides identification information for the cells and generates control signals for controlling the sorting of particles.

Typically in flow cytometers, the decision of whether to sort or not to sort a particle is made in hardware with approaches such as using lookup tables. For example, a lookup table may be implemented as a bit map in two dimensions corresponding to two measured quantities of interest such as forward scatter and different types of fluorescence, where the bit-position corresponding to a particular data point on the Cartesian plane is turned on if it is within a region of interest, and off otherwise. While efficient, lookup table based methods implemented in hardware are generally not sufficiently flexible to accommodate arbitrary user defined regions of interest of high resolution and high dynamic range data. From an implementation standpoint, look up tables may limit the sort logic to the use of AND gates. Further, the sort selection is typically limited to the two dimensional selections found on an X-Y graph available on a typical oscilloscope. Lookup tables, due to the down sampling required to implement tables of sizes such as 256×256 bits, may also limit the resolution of the data available for sortPage decisions when compared to the high resolution, high dynamic range data available from most flow cytometers. Implementation in hardware of an arbitrary range of regular expressions upon which to sort would be prohibitive in design complexity.

Since flow cytometers operate at very high speeds, it is necessary for the electronics systems to also operate at very high speeds while still being very accurate with high resolution and high dynamic range. Therefore, what is needed is a method and system for software sorting for flow cytometry.

SUMMARY OF THE INVENTION

In one embodiment, the present invention provides computer-implemented methods of sorting particles from a particle stream in a flow cytometer. The methods include receiving a sort logic definition; receiving raw event data values from the flow cytometer; calculating one or more sort decision making parameters using the raw event data values, and the sort logic definition; performing sort logic computations using the sort logic definition and the one or more sort decision making parameters to generate one or more sort decisions; converting the one or more sort decisions into one or more sort commands; and sending the one or more sort commands to the flow cytometer. The performing of sort logic computations may include algorithmically using conditional branching logic. In some embodiments, sort logic computations include using sort logic equations. The sort logic equations may include mathematical functions characterizing one or more regions of interest in multidimensional data space. Such mathematical functions may be determined based on one or more parameters provided by the user.

Another embodiment provides a method of sorting particles from a particle stream in a flow cytometer responsive to a computer-implemented sorting method. The methods include, obtaining raw event data values generated based on particles in the particle stream; sending the raw event data values to a computer; receiving one or more sort commands from the computer; sorting the particles according to the one or more sort commands; and sending one or more sort verification status values to the computer.

Another embodiment provides systems for sorting particles from a particle stream, having a flow cytometer and a computer coupled to the flow cytometer. The computer includes: an input that receives a sort logic definition from a user; a sort parameters module that calculates one or more sort decision making parameters based on raw event data values received from the flow cytometer and the sort logic definition; and a sort decision module wherein the sort decision module determines one or more sort decisions by performing sort logic computations using the sort logic definition and the one or more sort decision making parameters, and wherein the sort decision module converts the one or more sort decisions into one or more sort commands and sends the one or more sort commands to the flow cytometer. In another embodiment, the computer may also include an event status and storage module and wherein the event status and storage module stores sort decisions and corresponding sort status and verification data.

Yet another embodiment provides computer program products having a computer usable medium having control logic therein for causing a computer to sort particles from a particle stream in a flow cytometer. The control logic includes: a first computer readable program code that enables the computer to calculate one or more sort decision making parameters based on raw event data values sent from the flow cytometer and a sort logic definition; a second computer readable program code that enables the computer to make sort decisions by performing sort logic computations using the sort logic definition and the one or more sort decision making parameters;

and a third computer readable program code that enables the computer to convert the decisions regarding particle sorting into one or more sort commands and sends the one or more sort commands to the flow cytometer. In another embodiment, the control logic may further include computer readable program code that enables the computer to store sort verification status values with the corresponding sort commands and the corresponding raw event data values.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

Figure 1:
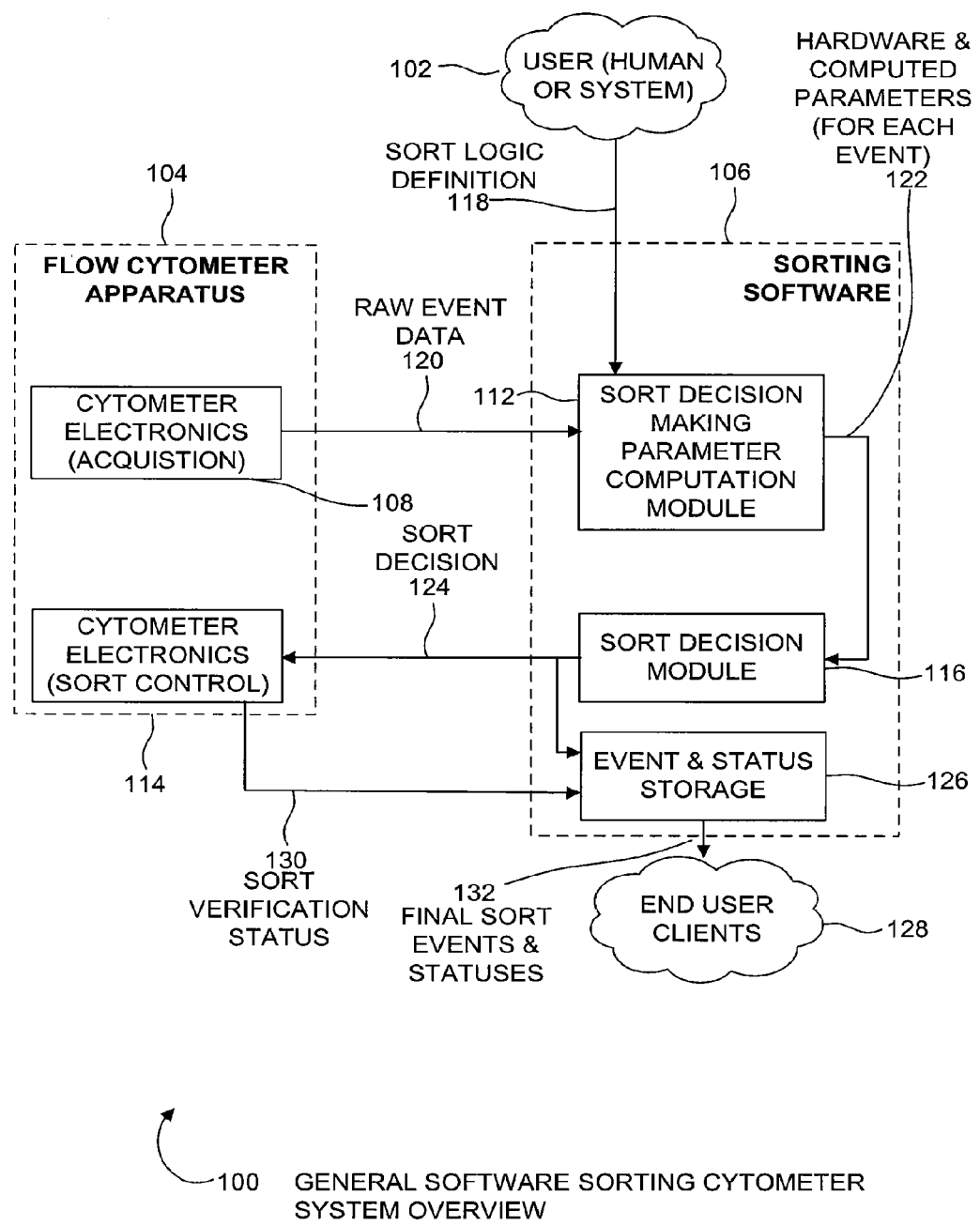
FIG. 1 is a schematic illustration of a general system overview for a software sorting flow cytometer system.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION OF THE INVENTION

Flow cytometers have been in clinical and research use for many years. Basically, the systems act to position small amounts of a substance, such as cells or other particles, within a sheath fluid. This sheath fluid may either form droplets or may exist in a jet (i.e., a continuous stream) for optical analysis. Through hydrodynamic focusing and laminar flow, the substance is split into individual cells or other particles and is surrounded by a sheath fluid. The particles may be multicellular organisms, cellular aggregates, viable cells, dead cells, cell fragments, organelles, large molecules, beads, viral particles, etc. In many applications, the sheath fluid together with its entrained substance is directed through and channeled by a nozzle and then exits the nozzle in a jet. Upon exiting the nozzle with the sheath fluid, the entrained substance either free falls or is channeled in an optically transparent pathway for analysis. The nozzle may also be set up so as to vibrate the exiting fluid jet so as to separate the fluid stream into isolated droplets some distance downstream from the point of discharge from the nozzle. The resultant separated droplets adopt a spacing which is a function of the stream velocity and the vibration wavelength. The vibration wavelength may be a function of the frequency of an oscillating crystal used to time the vibrations. Droplets containing the target of interest are charged by a charging device. The charged droplets are directed between two charged deflection plates, which angularly deflect charged droplets. The deflected droplets are then collected in containers positioned in the path of falling deflected particles. Using software to compute the sort decisions as disclosed herein, offers a range of flexibility that may not be available in hardware. Software is used to implement sorting based on a arbitrary criteria specified in regular expression form, and may use complex logic including conditional branching and heuristic decisions.

FIG. 1 is a schematic illustration 100 of a general system overview for a software sorting flow cytometer system. At a high level, the software sorting flow cytometer system consists of two primary components, the flow cytometer physical apparatus 104, and the sorting software 106 used to calculate sort decisions 124. The flow cytometer apparatus 104 consists of the physical materials to receive a fluid stream, analyze the stream for particles, break the stream into small droplets, and separate the droplets into separate result streams. Some of the physical materials included in the cytometer apparatus 104 may include a nozzle to create a stream, laser to illuminate the stream to analyze the stream for particles, oscillating crystal to time the break off of droplets, electrically chargeable deflector plates to deflect droplets to the appropriate result stream, and electronics for data acquisition 108 and sort control 114. The sorting software 106 interacts primarily with the flow cytometer apparatus electronics for data acquisition 108 and sort control 114. The sorting software 106 runs on a computer. An embodiment may use a Personal Computer (PC) as the computer running the sorting software 106. Further, an embodiment may use a personal computer with multiple Central Processing Unit (CPU) cores to optimize speed of the sort calculations by increasing the priority of the sorting program for one or more of the CPU cores while keeping at least one CPU core available for operating system and other non-time dependent processes.

An embodiment may use a touch-screen interface for a Graphical User Interface (GUI) for interaction with a user 102. An embodiment may further use a second computer, which may also be a PC, to run the Graphical User Interface (GUI) that interacts with the user 102. The GUI computer and the sorting software 106 computer may communicate using a standard network connection, such as one Gigabit Ethernet. When a second computer is used to provide the GUI for the user 102, the sorting software computer may be included as an embedded computer. An embodiment may use an embedded PC as the embedded computer. An embodiment may use Microsoft Windows XP as the operating system for personal computers included in the system. An embodiment may connect the flow cytometer apparatus 104 to the computer running the sorting software 106 using a PXI interface. PXI is an acronym for PCI Extension for Instrumentation. PCI is an acronym for Peripheral Component Interconnect, which is usually included as the primary communications bus on a personal computer. Thus, the flow cytometer apparatus 104 may be directly connected to the primary bus of the computer running the sorting software 106 to ensure a high speed communications connection.

The flow cytometer apparatus 104 collects raw event data 120 using acquisition electronics 108. An event occurs when the flow cytometer acquisition electronics 108 determines that an identifiable particle is encountered in the input stream. The cytometer acquisition electronics send the raw event data to the sorting software 106 via the communications connection with the computer running the sorting software 106. In some embodiments the flow cytometer acquisition electronics 108 may preprocess the raw event data 120 delivered to the sorting software 106. Preprocessing may include performing some basic Boolean logic operations with data acquired from the flow cytometer 104 sensors. Preprocessing may further include performing some data filtering on data acquired from the flow cytometer 104 sensors. Preprocessing may also include performing data acquisition and processing so that the raw event data 120 is high resolution data. Preprocessing common calculations such as logic and filtering may increase the overall speed of the system processing because preprocessing permits the relatively higher speed data acquisition electronics to perform common calculations prior to delivering the raw event data 120 to the sorting software 106. Preprocessing the raw event data 120 to obtain higher resolution data permits more precise mathematical operations when the sorting software 106 uses the raw data values 120 to perform computations. The preprocessing for the raw event data 120 is disclosed in more detail in U.S. patent application Ser. No. 12/053,439, entitled "Multi-Gain Adaptive Linear Processing and Gated Digital System for Use in Flow Cytometry," which is specifically incorporated herein for all it discloses and teaches.

The software parameter computation module 112 receives the raw event data 120 from the flow cytometer acquisition electronics 108. The software parameter computation module 112 also receives the sort logic definition 118 from the user 102. The sort logic definition 118 may consist of an arbitrary user-defined equation of the intermediate calculations and the final sort logic equations desired to sort the particles found in the input flow stream. The user 102 may be a human user or the user may be an automated system that adjusts the desired sort logic definition 118 per some independently determined criteria. The software parameter computation module 112 calculates parameter values for parameters in the sort logic definition 118 that are calculated based on the raw event data 120. Calculated parameters may be based on raw event data values 120 sent by the flow cytometer apparatus 104, constant values entered by the user or stored as standards within the sorting software 106, and other calculated values. Thus, a calculated value may be many mathematical steps removed from the raw event data. For example, a region hit detection computed value might be four times removed from the raw event data the calculation is based upon, because a first calculated value may be the "fluorescent compensation" resulting from a linear equation, a second calculated value may be a ratio of the linear values of the first calculated value, a third calculated value may be a log of the ratio of linear values, and a fourth value may be the region hit detection calculated using the log value.

Once the software parameter computation module 112 calculates all computed parameter values, the raw and computed parameters for each event 122 are sent to the sort decision module 116. The sort decision module 116 plugs the raw and computed parameter values 122 into the sort logic definition sent by the user 102. The sort logic definition 118 contains a logic definition, for example, a Boolean logic definition, of the region of particles to sort. Boolean logic in a sort logic definition 118 is defined by a Boolean logic equation and not by a lookup or bitmap table. Thus, the sort logic definition 118 is capable of defining logic at many levels and permits conditional branching of logic as desired by the user 102. The sort logic definition 118, when implemented as Boolean logic equations, may further permit the region of particles to sort to include areas defined by equations of a conic section, regions defined in three dimensional space, and regions defined in multi-dimensional space (i.e., regions defined in four or more dimensional space). The calculation for the region of particles to sort is disclosed in more detail in U.S. provisional application Ser. No. 60/910,646 entitled "Method for Real-Time Algorithmic Discrimination of Flow Events within Desired Geometric Regions," which is specifically incorporated herein for all it discloses and teaches. Further details on receiving and using user provided definitions of regions of interest having clusters of particles to sort are described below with respect to FIG. 10.

The sort decision module 116 evaluates the sort logic definition, removes sort overlaps by selecting a single result stream to receive each encountered event, and creates the sort decision 124 to send to the cytometer sort control electronics 114. The sort decision 124 is sent to the sort control electronics 114 of the flow cytometer apparatus 104 as sort commands formatted for the flow cytometer apparatus 104. The sort decision 124 is also sent to the event and status storage 126 for use in reporting and analyzing sort operation and results.

The flow cytometer sort control electronics 114 sorts the drops broken off from the input stream into the proper output stream as defined by the sort logic decision 124. The flow cytometer sort control electronics 114 may not implement a sort decision 124 for a variety of reasons. For instance, if a sort decision is received after a particle has already passed the break off point, the sort control electronics 114 cannot sort the drop containing the particle. There may also be instances where the sort control electronics encounter some other fault that causes the system to be unable to sort a drop properly in accordance with the sort decision 124. Thus, the sort control electronics 114 may verify if all of the proper signals were sent to the flow cytometer apparatus 104 equipment to properly sort a drop. Another embodiment may further verify that a drop is sorted by using a camera to observe the break off portion of the cytometer apparatus 104 to observe that a drop containing a particle does in fact break off and go to the proper output stream. The sort control electronics 114 records whether a particle/event was properly sorted according to the sort decision 124 in the sort verification status value 130.

The sort verification status value 130 can be sent back to the sorting software 106 where it may be placed in the event and status storage area 126. The verification status and the sort decision are recorded together for each particle/event. The final events and statuses 132 may then be delivered to an end user client 128. The end user client 128 may be the same user 102 that entered the sort logic definition. There may be multiple end user clients 128 that access the system to receive the final sort events and statuses. The multiple end user clients 128 may access the event and status storage 126 over a local or network communication connection. The multiple end user clients 128 may further access the event and status storage 126 over the Internet using a dedicated interface application or using web pages delivered by the system in response to an Internet web browser application.

Another feature that may increase overall system performance is Intellisort. Intellisort automatically adjusts the system to permit the flow cytometer apparatus 104 to have a more stable drop and to maintain a stable drop delay. Intellisort is a system that uses a camera to monitor the drop break off point of the stream in the flow cytometer apparatus and compare the current image profile of the break off point to an initial image profile recorded at the time the drop delay was initially calculated. If the current image profile of the break off point differs from the image profile at the time the drop delay was initially calculated, the flow cytometer apparatus is sent commands to adjust the system to return to the state of the system when the initial image profile was recorded. The Intellisort system is disclosed in more detail in the disclosure with respect to FIG. 7 and in even more detail in U.S. provisional application Ser. No. 60/926,268 entitled "Apparatus, Method and System for Controlling Drop Delay Time in a Flow Cytometer," which is specifically incorporated herein for all it discloses and teaches.

Figure 2:
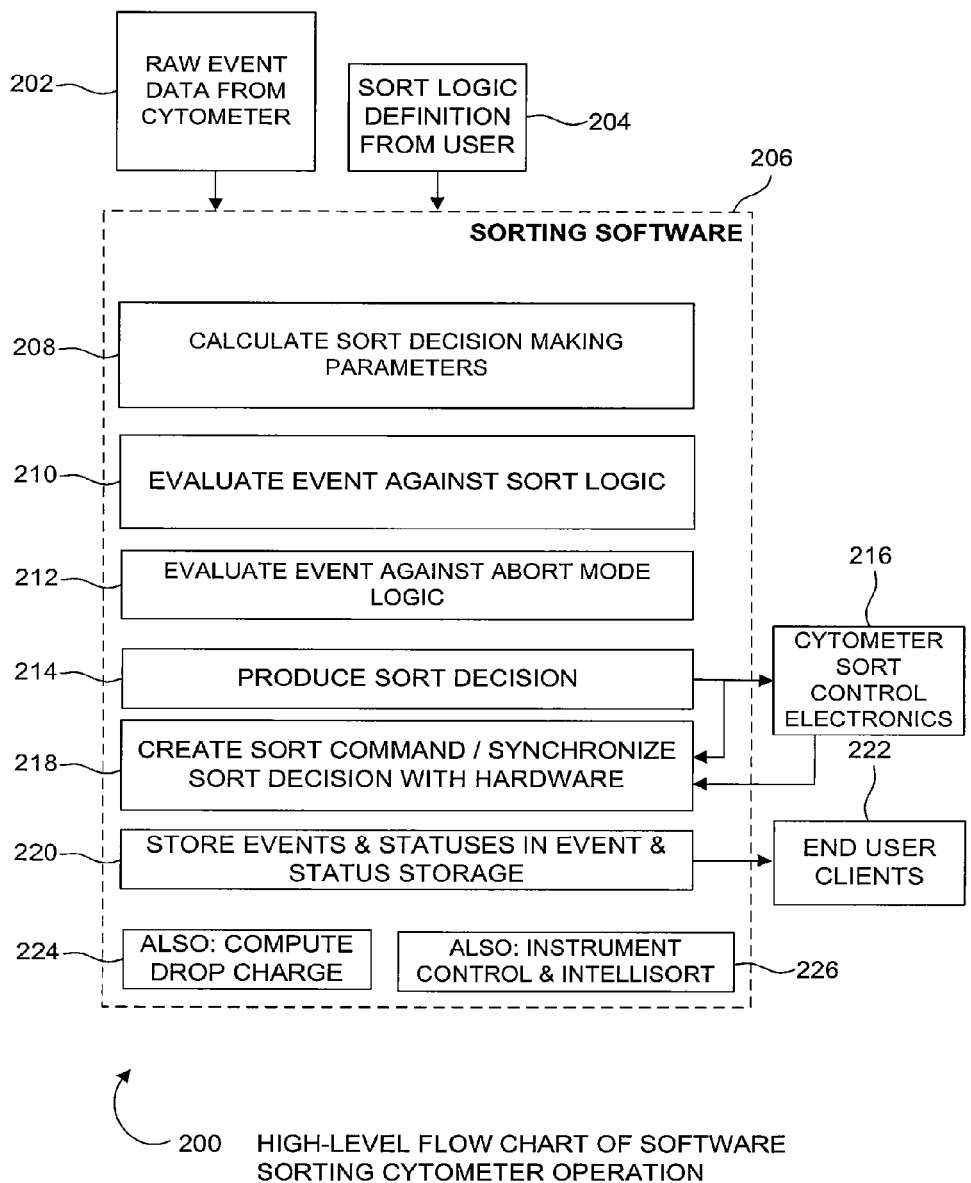
FIG. 2 is a high level flow chart of the operation of a software sorting flow cytometer.

FIG. 2 is a high level flow chart 200 of the operation of a software sorting flow cytometer. The software sorting processing module 206 receives the raw event data 202 and the sort logic definition 204 as inputs to the software sorting process. The raw event data 202 is supplied by the acquisition electronics of the physical flow cytometry apparatus. The raw event data 202 may be preprocessed by the flow cytometer acquisition electronics to perform basic Boolean logic functions and/or to perform filtering on the data obtained from the flow cytometer sensors in order to increase speed on commonly performed functions. The raw event data 202 may also be preprocessed to increase the resolution of the data obtained from the flow cytometer sensors in order to increase the precision of the calculations in the sorting software 206. The sort logic definition 204 may be provided by a user of the system. A user need not be a human, but may be an automated system that determines sort logic based on the programming of the automated system. The sorting software processing code 206 performs computations on the raw event data 202 at step 208. The computations include user defined calculated parameters contained in the sort logic definition 204. A computed parameter may be based on raw data values, constant values, or other computed values. Some examples of computed values include compensation values, zoom values, log values, and other similar computations.

The computations are performed for each event/particle encountered by the flow cytometer apparatus. The software sorting processing module 206 then evaluates the event/particle raw and computed data against the sort logic at step 210. The evaluation of the sort logic may include algorithmic discrimination of regions, including conditional branching logic to permit the sort logic to implement logic that may not be implemented using a lookup/bitmap table. The sorted regions may be a wide variety of shapes including: conic sections, three dimensional regions, and multi-dimensional regions. The sorting software processing module 206 then evaluates many of the events/particles against abort mode logic at step 212 and produces a sort decision at step 214. The sort decision can be sent to the sort control electronics 216 of the flow cytometer apparatus and the sort decision may be synchronized 218 with the cytometer apparatus hardware. At step 220 the sort decisions and verification statuses are stored, for example, in the event and status storage area on the computer. The sort decisions and verification statuses are available to end user clients 222 for analysis and reporting on sort operations. Multiple end user clients 222 may access the system concurrently using a network connection. The network connection may be an Internet connection and the multiple end user clients 222 may be accessing the system using a web browser.

The sorting software processing module 206 may also compute the necessary drop charge 224 or parameters necessary for the flow cytometer 104 to compute the required drop charge to deflect the drop into the desired result stream. Further, the sorting software processing code 206 may implement drop and drop delay stabilization 226 such as that, for example, described with respect to the disclosure for FIG. 7.

Figure 3A:
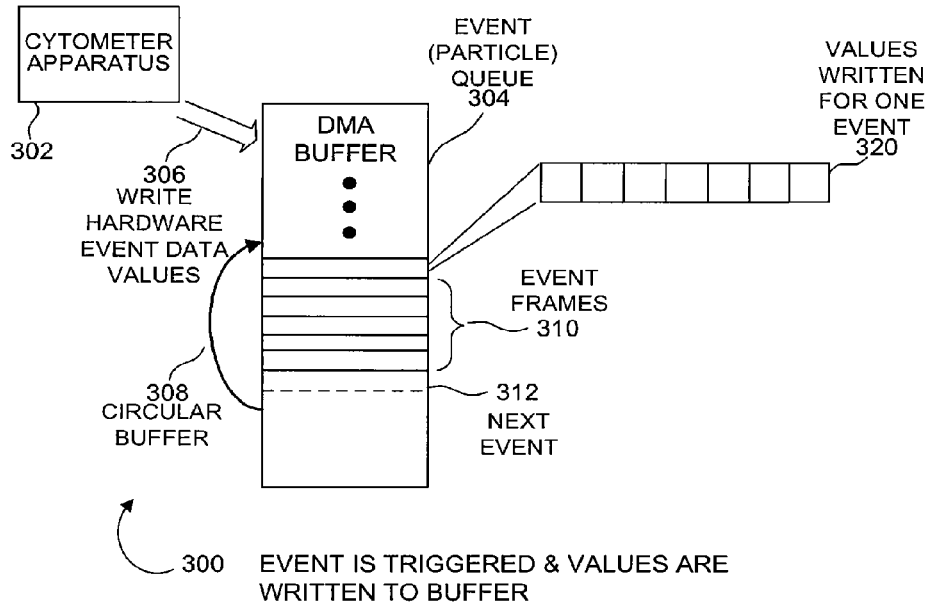
FIG. 3A is a schematic illustration of the communication and buffer operation when an event is triggered and raw values are written to the event buffer in one embodiment.

FIG. 3A is a schematic illustration 300 of the communication and buffer operation when an event is triggered and raw event data values 306 are written to the event buffer 304. When the flow cytometer apparatus 302 encounters an event/particle, the cytometer 302 writes the raw event data values 306 to the event/particle queue 304. For the embodiment disclosed with respect to FIG. 3A, the event/particle queue 304 may be implemented using a Direct Memory Access (DMA) memory buffer. A DMA buffer permits fast reading and writing of data values. The DMA buffer of the event/particle queue 304 holds a plurality of event frames 310. Each event frame 320 contains data for a single event/particle. The event/particle queue works as a circular buffer 308. The next event frame to be written 312 progresses down the queue until the last memory entry in the buffer is reached, then the circular buffer 308 moves the next event frame to be written 312 to the top of the memory DMA buffer. After the first pass through the DMA buffer, old data in the next event frame 312 may be overwritten with newly acquired data.

Figure 3B:
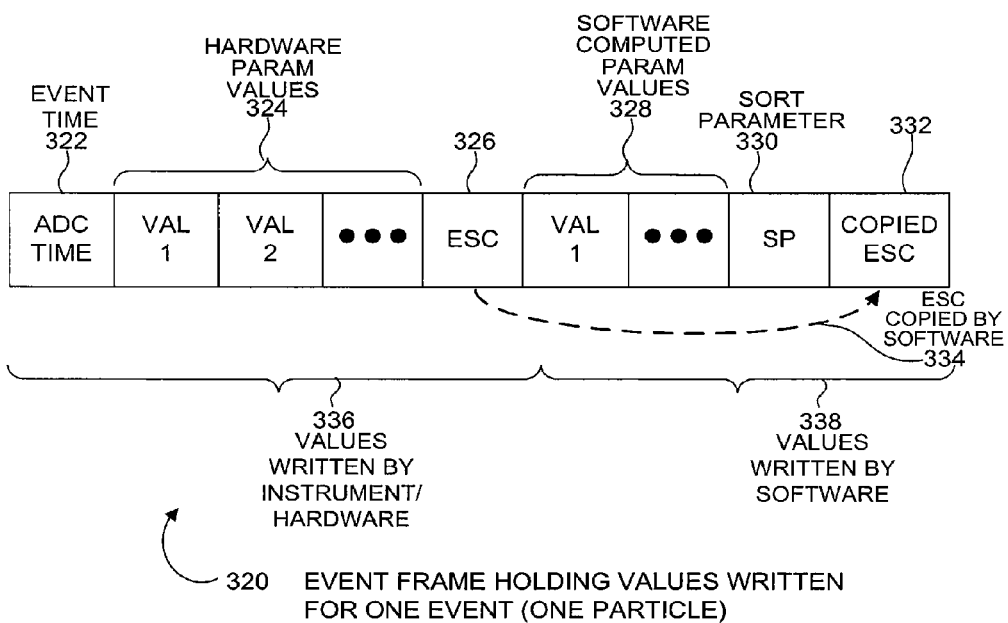
FIG. 3B is a schematic illustration of an exemplary event frame holding values written for one event (i.e., one particle).

FIG. 3B is a schematic illustration of an event frame 320 holding values written for one event (i.e., one particle). The event frame 320 stores the sort decision making parameters used by the sorting software to make the sort decision. Each parameter may be stored within a register in the event frame. A parameter register is typically a 16 or 32 bit data value, but may be larger or smaller as needed. The event frame may be broken down into two sections, registers for storing parameter values written by the flow cytometer apparatus instruments and hardware 336 and registers for storing parameter values computed and written by the sorting software 338. Values written by the instrument/hardware 336 include: the Analog-to-Digital Converter (ADC) time 322, one or more raw data values 324, and an "esc" event status and count indicator 326. The ADC time 322 is the time equivalent to the time the particle was detected by the flow cytometer sensors. The ADC time 322 may also be referred to as the event time 322. In the embodiment shown, the ADC/event time 322 is a 64-bit value that represents when the event/particle occurred. The ADC/event time 322 may be divided by the oscillating crystal frequency of the flow cytometer apparatus to compute the "drop index." The "drop index" indicates the location in drops relative to the ADC/event time where an event/particle was found. It is possible for multiple events/particles to appear in a single drop.

A "drop delay" may be added to the drop index to locate the drop at the break off point of the flow cytometer apparatus 302 in order to compute the "final drop index." The "drop delay" is needed because the event/particle is located by the laser before the input stream is broken off into drops. The input stream falls a small distance after passing the laser before being broken into droplets. The drop delay, which may be measured in fractions of drops, indicates the time delay, in number of drops passed, before the event/particle will be broken off into a droplet.

Values written by the sorting software 338 may include: software computed parameter values 328, the sort parameter 330, and the final "esc" 332. The software computed parameter values 328 may include constant values and computed values. The sort parameter 330 may be a 32-bit value that describes how an event/particle was sorted and verified. The sort parameter 330 may be written by the software after the sort decision is made and after the event/particle was actually sorted. The "esc" register 326 includes event status counts for an event. The "esc" register 326 may be completed when the event/particle is fully processed. The "esc" register 326 may be copied by the sorting software 334 to the "copied esc" register 332 for ease of access when working with values written by the sorting software 338. The completed event frame, including status values, may be copied to the event and status storage after the event is fully processed. The events and statuses stored in the event and status storage may be available to one or more client applications, such as multiple GUIs that may be accessing the system over the Internet. The GUI may be a dedicated application or the GUI may be implemented as one or more web browser pages.

Figure 3C:
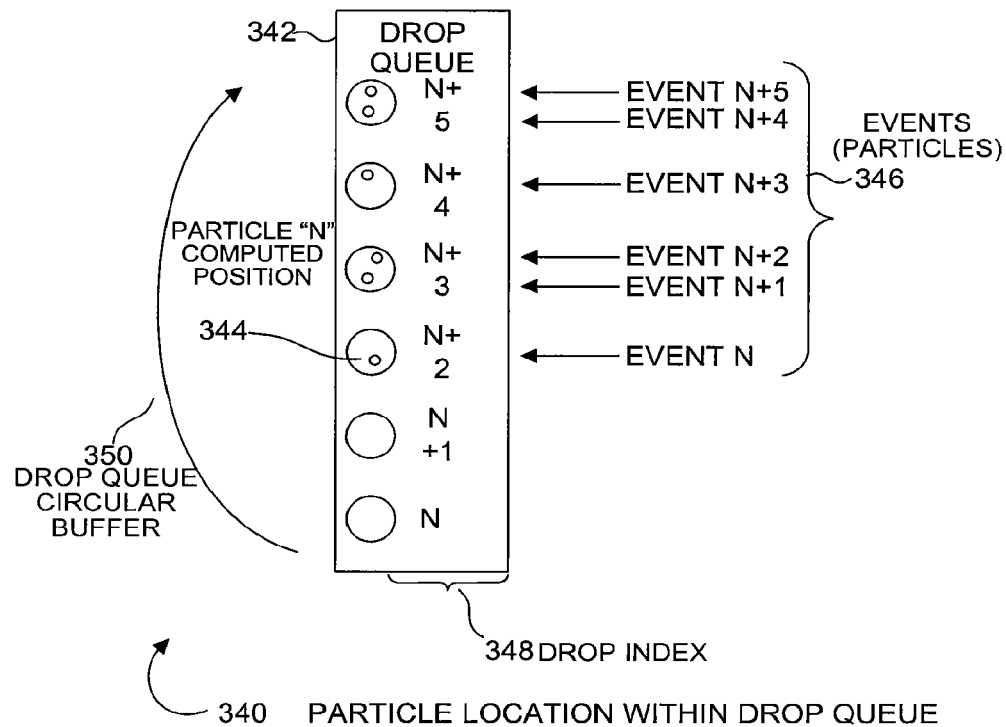
FIG. 3C is a schematic illustration of a drop index and the relation to events found in the drops.

FIG. 3C is a schematic illustration 340 of a drop queue and the relation to events found in the drops. The ADC/event time 322 may also be used to compute the relative position within an absolute drop (i.e., the drop containing the event/particle). The position within the absolute drop is indicated by an "absolute drop index." The drop queue 342 is a representation of the physical drops that will be broken off by the flow cytometer apparatus 302. Similar to the event/particle queue 304, the memory used to store the representation of the drop queue 342 may be treated as a circular buffer 350, so when the software reaches the end of the buffer, the software returns to the start of the buffer and overwrites old data. Each drop may be indexed by the "drop index" 348. The "drop index" is a relative marking of the location of a drop in relation to other drops. For FIG. 3C, the drop N is the reference drop and drops N+1 to N+5 are drops coming after N by the number of drops added to N. Drops preceding N would be indicated by N minus the number of drops that the drop in question precedes drop N. Events/particles 346 do not necessarily line up one per drop. Multiple events/particles may appear in a single drop, one event/particle may appear in a single drop, or no events/particles may appear in a single drop. For the situation in FIG. 3C, drops N and N+1 contain no events/particles. Drop N+2 contains event N, drop N+3 contains events N+1 and N+2, drop N+4 contains event N+3, and drop N+5 contains events N+4 and N+5. The software working on event N computes 344 the "absolute drop index" to locate the position of event/particle N within drop N+2. As each event's location is computed within the event's absolute drop index, a map of all the events and their locations is created for the drop queue.

Figure 3D:
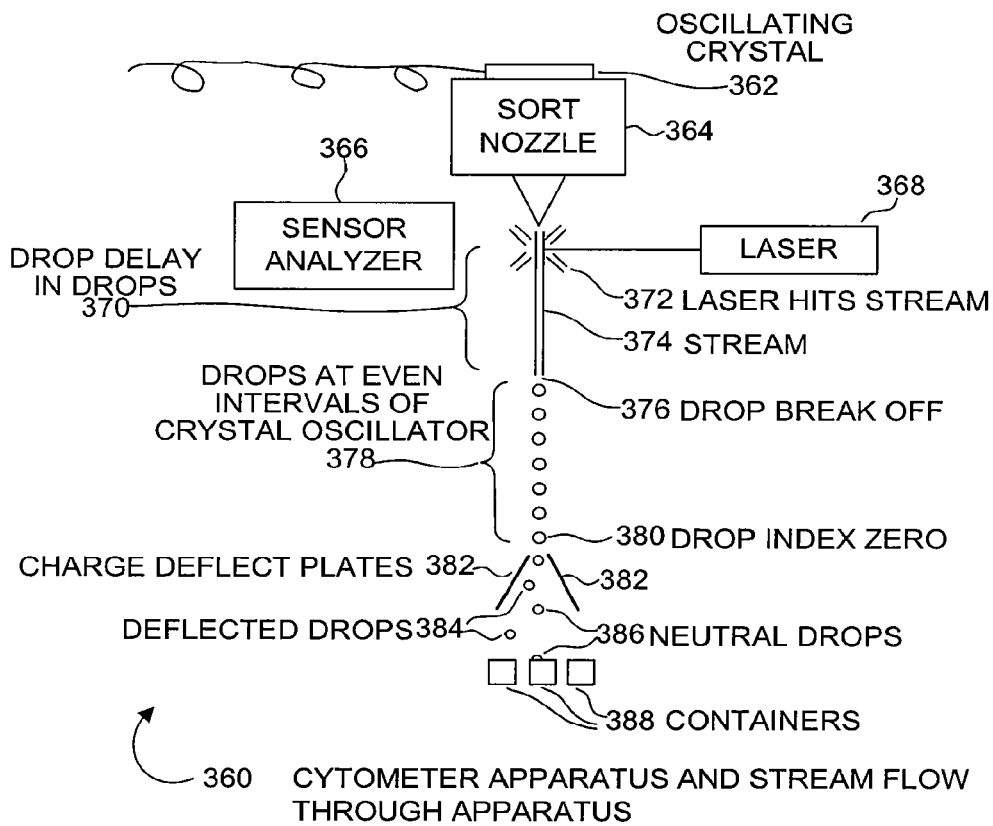
FIG. 3D is a schematic illustration of the physical apparatus and stream flow for a flow cytometer apparatus in one embodiment.

FIG. 3D is a schematic illustration 360 of an exemplary physical apparatus and stream flow for a flow cytometer apparatus. The input flow stream 374 is dispensed by the sort nozzle 364. The oscillating crystal 362 causes the sort nozzle to vibrate such that drops break off the stream at even intervals 378. Prior to the drop break off point, the laser 368 illuminates the stream and sensors and analytical equipment 366 sense the illumination given off by the laser illuminated input stream 374 and analyze the stream 374 for events/particles. The detection of a particle by the sensor/analytical equipment 366 triggers an event in time. The drop delay 370 is the time measured in drops for a particle to fall from the point where the laser hits the stream 372 to the point where the droplets break off 376. The drop delay may be measured down to a fraction of a drop (e.g., drop delay of 37.8 drops). Drops 378 contain all events/particles that occurred during the period of time the stream 374 that makes up each drop 378 was illuminated 372 by the laser 368. For instance, drop index zero 380 contains all events from "time zero" to "time zero" plus one frequency cycle for the oscillating crystal. The sort nozzle system 364 may also charge the stream 374 at the time each drop 378 is broken off 376 such that each drop 378 receives a specific charge prior to breaking off 376 from the stream 374. The sort nozzle system 364 is capable of changing the charge on the stream 374 as each droplet 378 breaks off so that each drop 378 may have a different charge from all of the other drops 378. The charge deflection plates 382 are given an electrical charge that will cause charged drops 384 to deflect rather than falling straight down. As the drops fall through the charge deflection plates 382, the charge applied to the drops 378 at the break off point 376 interact with the charge of the deflection plates 382 to cause drops to deflect into various containers 388. In FIG. 3D, depending on the charge, drops may be directed to one of three containers 388. Positively charged drops may go to one side and negatively charged drops may go to the other side. Neutrally charged drops 386 will fall straight down into the middle container 388. In other embodiments the amount of positive or negative charge may be varied to permit result streams to go into more than three containers. For instance two containers on the positive side and two containers on the negative side plus the neutral container to obtain five result streams.

Figure 4A:
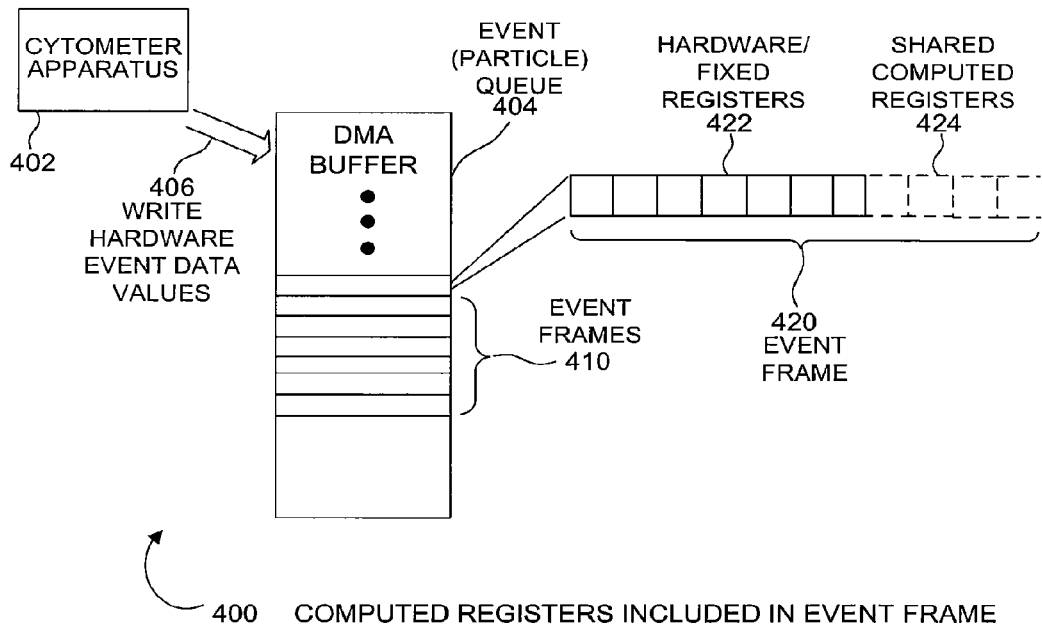
FIG. 4A is an exemplary schematic illustration of computed, or calculated, registers included in an event frame.

FIG. 4A is a schematic illustration 400 of computed, or calculated, registers included in an event frame. The flow cytometer apparatus 402 writes raw event data values 406 for events/particles to the DMA buffer of the event/particle queue 404 whenever an event/particle is detected. The information for each event/particle may be stored in the event frames 410 of the DMA buffer 404. Each event frame 420 will need to hold both raw and computed values. The number of raw event data values 406 that may appear in an event frame may be fixed to the raw data values that the flow cytometer apparatus 402 is capable of sensing. Adding sensors for additional information (e.g., ambient temperature, barometric pressure, etc.) may increase the number of raw event data values available from the flow cytometer apparatus 402, but the number of raw event data values will not change between runs. There may also be some other fixed values such as the "esc" event status and count register and the sort parameter status register that may also be incorporated as fixed registers since the registers will be used in the event frame every run, regardless of the user-defined sort logic definition which includes the various user-defined computations involved in the sort logic definition. Each event in the event queue may be minimally sized to store all of the raw/fixed data registers 422. The DMA buffer 404 itself should be large enough to handle events until the events are fully processed before a subsequent event overwrites the event data. To accommodate the additional memory space needed to store the computed optional registers 424, the event frame written 406 by the cytometer 402 could be sized to account for the additional computed data registers. Another option may be to size the frame 406 to only the size of the raw and other fixed values 422 when writing 406 from the cytometer 402, but leave extra space on the end of each frame 420 in the DMA buffer. Using either method, the system may either make the computed data registers 424 a fixed size allowing only a specific number of computed data registers 424 or re-dimension the event frames 410 in the DMA buffer 404 and/or on the cytometer 402 each time the number of computed registers 424 changes, which may happen every run.

It may be complex and computationally inefficient to re-dimension the DMA buffer 404 for each run as compared to having a fixed size for the DMA buffer 404. The computed values may not be needed after a tentative sort decision is reached for the frame. The tentative sort decision may be made in a time frame such that the computed registers 424 can be used for one event frame and then overwritten for use by the next event frame. Thus, only one set of computed registers 424 is necessary to accommodate all the event frames 410 in the event queue 404. By sharing the computed registers 424, the system need not re-dimension the entire event queue for each run. The one frame's worth of computed registers needed to support the tentative sort decision may be easily resized at runtime without a significant amount of effect on other components or overall memory usage.

Figure 4B:
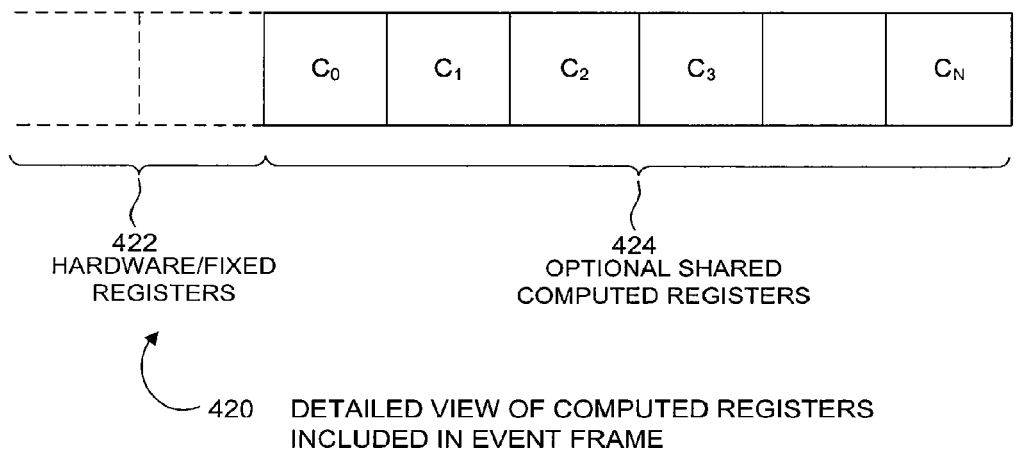
FIG. 4B is an exemplary schematic illustration of a detailed view of the computed registers in an event frame.

FIG. 4B is a schematic illustration of a detailed view of the computed registers in an event frame 420. The computed registers 424 are shared among the event frames. Basically, each frame appends the shared computed registers 424 to the raw/fixed registers 422 of the event frame 420 while the event frame 420 is being used in the tentative sort decision process. Once the event is no longer part of the tentative sort decision process, the next event appends the computed registers 424 to the next event's raw/fixed registers 422 for tentative sort decision processing. Computations included in the computed registers 424 may be user-defined computations. Computations may be based on raw values, constant values, other system values such as those provided by external sensors, or other computed values for the event frame 420. External sensors may include sensors for things such as temperature, air pressure, humidity, etc. Parameters and results may be modified at runtime based on changes in populations of various particles seen during the run. The runtime changes include dynamically optimizing/updating the sort logic as well.

Figure 5A:
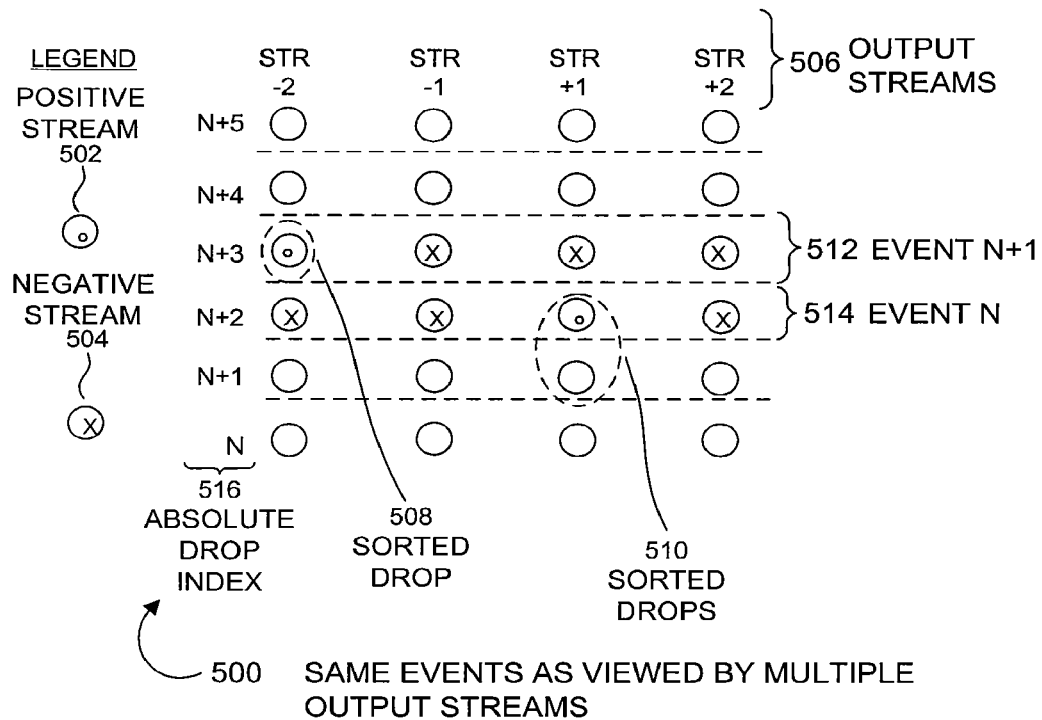
FIG. 5A is an exemplary schematic illustration of events in the input stream as viewed by multiple output streams.

FIG. 5A is a schematic illustration 500 of events in the input stream as viewed by multiple output streams. When an event is "seen" by the flow cytometer apparatus, it maybe positive 502 for more than one output stream 506. For multiple output streams 506 a separate drop queue (STR−2, STR−1, STR+1, and STR+2) is maintained for each output stream 506. The drop index for each output stream may be the absolute drop index 516, which corresponds with time. The events 512, 514 for each output stream 506 are the same for all output streams. Thus, event N (514) and event N+1 (512) are the same for all drop queue's (STR−2, STR−1, STR+1, and STR+2). For each output stream 506, the events 512, 514 are viewed in the context of the sort logic for each output stream's 506 drop queue (STR−2, STR−1, STR+1, and STR+2). Thus, it is possible for one output stream 506 to indicate that an event is positive 502 while another stream 506 indicates that an event is negative. For instance in FIG. 5A, event N (514) is positive 502 for drop queue STR+1, but negative 504 for drop queue STR−1. The initial indication of positive 502 or negative 504 is determined by the "tentative" sort decision derived from the user-defined sort logic definition including user-defined computed parameters. The tentative sort decision is determined per event 514 and per stream (STR−2, STR−1, STR+1, and STR+2). Hence the tentative sort decision does not consider other events 512.

When enough time has passed that the sorting software knows about events in nearby drops, the "final" sort decision may be completed. While the tentative sort decision is per event the final sort decision is per drop. Thus the final sort decision for STR−2 would sort drop N+3 (508). The final sort decision for STR+1 would sort drops N+2 and N+1 (510). Particles may move up or down in the drop stream based on a variety of calibration settings, such as stream input equipment, nozzle equipment, stream characteristics, etc. For the drops shown in FIG. 5A, it is assumed that the calibration settings result in a potential +/− one quarter drop shift for detected particles (events). Therefore, the sorting of drop N+1 in STR+1 may be necessary because particles may, for example, move +/− one quarter of a drop, and event N (514) which is in the leading quarter of drop N+2, may have moved to the previous drop N+1.

The final sort decision may further be based on one or more user configurable options including the following:
  (a) Sort Envelope: The sort envelope determines the number of drops the user is willing to sort in attempting to ensure that a desired event is sorted. For the 0.5 envelope the whole drop is sorted, but the event must occur near the drop center. For the 1-2 envelope either one or two drops are sorted depending on the placement of the event within the drop. If the event is close to the edge of the drop, the neighboring drop will also be sorted.
  (b) Sort Mode: The sort mode determines the purity of the sorted output. The sort mode configuration allows the user to tradeoff the purity and the concentration of the collected sorted output based on the likelihood of contaminant in the sorted output. Three sort modes may be defined, including:
    1. Single: Only one positive event 502 in the drop
    2. Purify: Only positive events 502 in the drop
    3. Enrich: All positive events 502, negative events 504 are tolerated
  (c) Sort Precedence: In the case where the same drop is selected to be sorted into more than one output stream 506, the sort decision overlaps multiple output streams 506. The drop may only be sorted into at most one output stream 506. To resolve conflicts, the sort software automatically considers "single" sort mode streams before "purify" sort mode streams, and "purify" sort mode streams before "enrich" sort mode streams. The user may designate which streams have higher priority among streams that have the same sort mode. The actual stream selected to receive the sorted drop is flagged so that it is possible to "overlap" sort decisions with sort logic on future drops. Thus, the system is capable of logically selecting which stream a drop goes in based on past "overlap" decisions. In this way, the system is capable of providing higher yields and faster sort rates while still providing sophisticated "overlap" sort decisions.

Figure 5B:
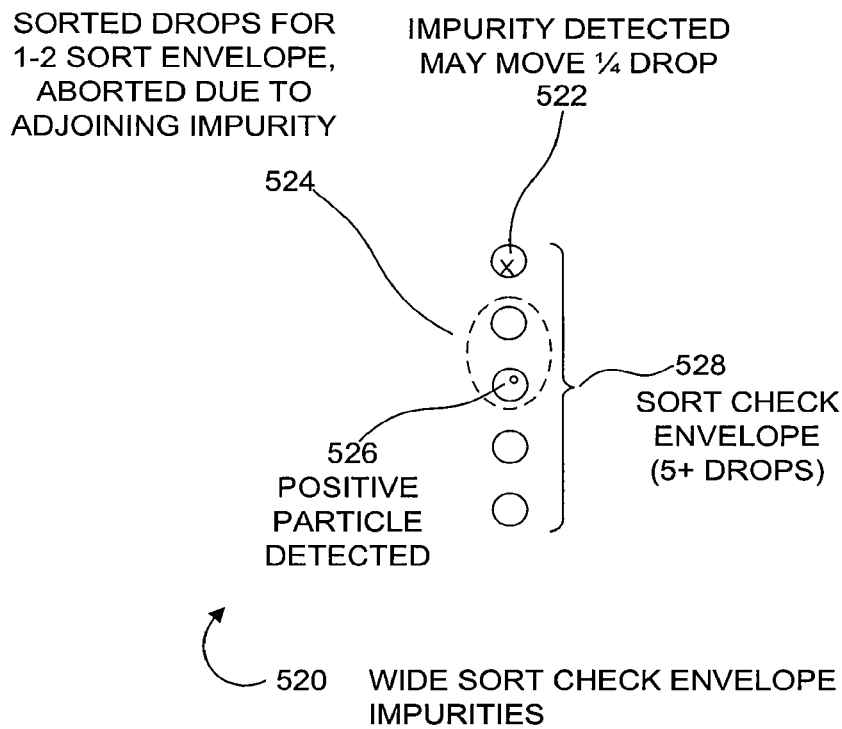
FIG. 5B is an exemplary schematic illustration of a wide (i.e., 5 drop) sort check envelope to filter out potential impurities.

FIG. 5B is a schematic illustration 520 of a wide (i.e., 5 drop) sort check envelope to filter out potential impurities. The sorting software may consider a larger sort envelope than the maximum sort envelope available to the user. In the embodiment shown in FIG. 5B, the maximum sort envelope is three drops. Thus, the sort check envelope 528 considers at least five drops to determine which drops to sort. Drops considered would generally be an equal number of drops before and after drops selected for sorting 526. In the case of FIG. 5B, for a 1-2 sort envelope in single mode, a sort decision is made to sort two drops 524, 526 when the positive particle 526 is near the trailing edge of the drop so that both the positive drop 526 and the subsequent drop are selected for sorting. If the drop succeeding the last drop selected to be sorted 524 contains a negative particle 522 near the leading edge of the drop, the sorting software will abort the sort selection because of the possibility for contamination. Note that in the diagram new drops appear at the top and old drops appear at the bottom of the diagram as the drops are falling downward. Thus, a subsequent drop would appear above the reference drop. Particles may move up or down in the drop stream based on a variety of calibration settings, such as stream input equipment, nozzle equipment, stream characteristics, etc. For the system in FIG. 5B, it is assumed that the calibration settings result in a possible shift of a particle by +/− one quarter of a drop. By expanding the sort check envelope 528, the sorting software increases the purity of the resulting sort stream.

Figure 6:
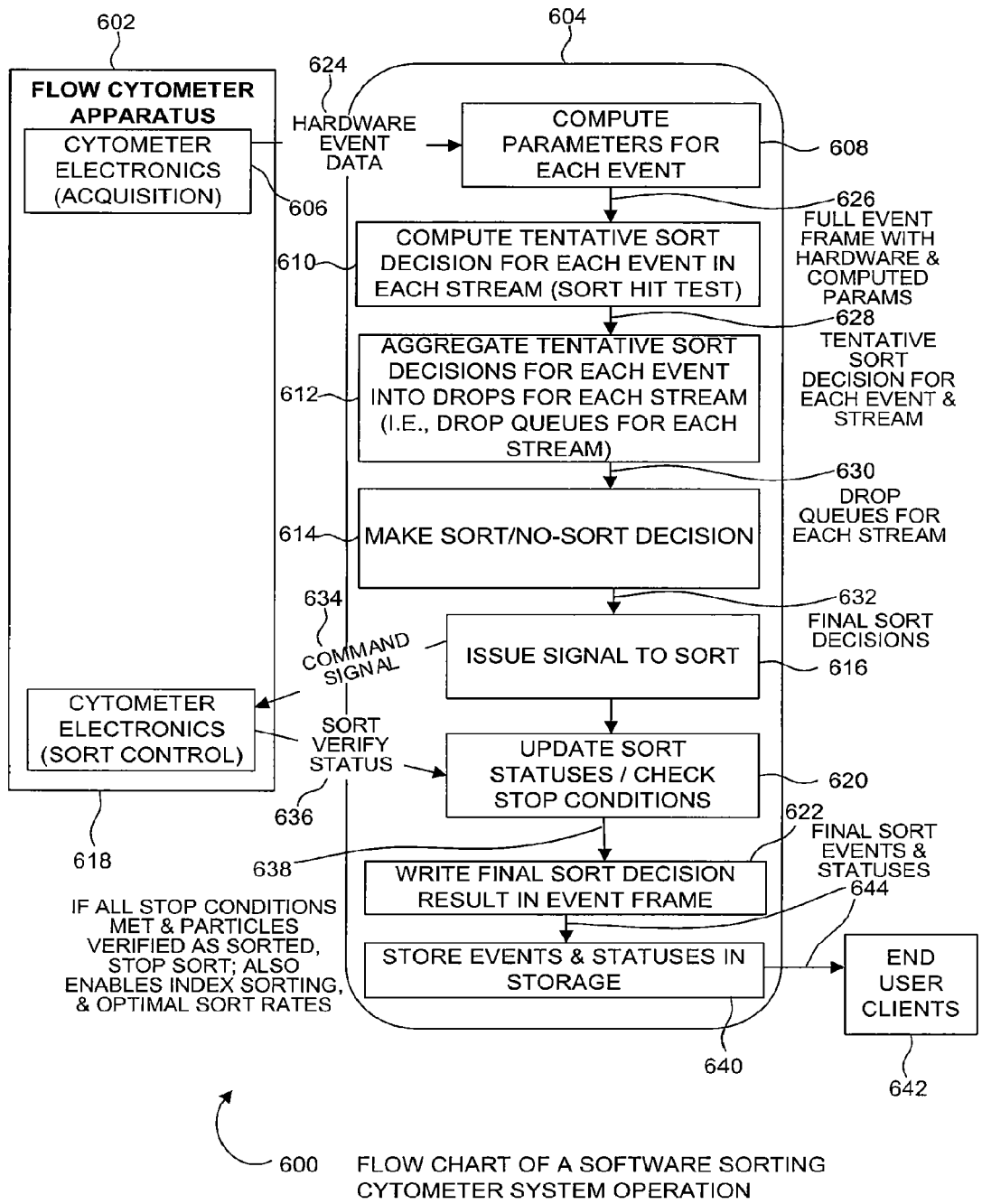
FIG. 6 is a lower level flow chart of the software sorting flow cytometer system operation in one embodiment.

FIG. 6 is a lower level flow chart 600 of the software sorting flow cytometer system operation. The flow cytometer apparatus 602 acquires the raw event data 624 in the cytometer acquisition electronics 606. The raw event data 624 may be preprocessed by the flow cytometer acquisition electronics 606 to perform basic Boolean logic functions and/or to perform filtering on the data obtained from the flow cytometer 602 sensors in order to increase speed on commonly performed functions. The raw event data 624 may also be preprocessed to increase the resolution of the data obtained from the flow cytometer 602 sensors in order to increase the precision of the calculations in the sorting software 604. The raw event data 624 is sent to the sorting software 604. The sorting software 604 runs on a computer. The computer may be a PC (personal computer) and may further be a PC server. The sorting software may also be burned onto a firmware device such that the software is stored and executed on the firmware device. One example of a firmware device is a Field Programmable Gate Array (FPGA) device burned to run the software sorting program. Using a burned firmware device may be especially useful for portable devices where an embedded computer maybe too bulky for practical purposes.

After the sorting software 604 receives the raw event data 624, the sorting software 604 computes any additional sorting decision making parameters for each event 608. The full event frame, including raw and computed parameters 626, is then used to compute a tentative sort decision for each event in the stream at step 610. Step 610 may also be referred to as a sort hit test. The evaluation of the sort logic may include algorithmic discrimination of regions, including conditional branching logic to permit the sort logic to implement logic that may not be implemented using a lookup/bitmap table. The sorted regions may be a wide variety of shapes including: conic sections, three dimensional regions, and multi-dimensional regions. The tentative sort decision for each event and for each stream 628 may then be used to aggregate the tentative sort decisions for each event into drops for each stream at step 612. That is, the sorting software creates the drop queues for each stream with each event's tentative sort decision indicated in the drop queue. The drop queues for each stream 630 are then used to make a sort/no-sort decision 614. A drop may be sorted into, at most, one output stream. The choice of which stream may be determined in the manner described in the disclosure with respect to FIG. 5A.

The sort decision is also subject to sort abort logic to limit the possibility of including contaminants in output streams that do not want contaminants. The sort abort logic is described further in the disclosure with respect to FIG. 5B. The final sort decision 632 is then issued as a signal for execution on the cytometer hardware 602. A sort command signal 634 is sent to the cytometer apparatus 602 where the sort command 634 is received by the cytometer sort control electronics 618. The cytometer sort control electronics 618 performs the sort commands 634 and sorts the appropriate drops. The cytometer sort control electronics 618 may not sort a drop for many different reasons. One potential reason for missing a drop may be because the sort decision took too long to reach the cytometer sort electronics 618 and the sorted drop has already passed the break off point. The sort control electronics 618 may monitor a drop to ascertain whether or not the drop was sorted according to the corresponding sort command. Another embodiment may take monitoring for missed drops a step further by employing a camera to watch the stream at the break off point and then analyzing the video image to determine if a drop "actually" breaks off and goes into the proper receptacle. Whether a camera is used or not, the cytometer sort control electronics 618 may have knowledge as to whether each drop dropped or did not drop. The cytometer sort control electronics 618 sends a sort verification signal 636 back to the sorting software 604 to indicate whether the cytometer sort control electronics 618 has determined if a drop was or was not properly sorted.

The sort verification signal 636 may be received by the sorting software 604 where the sort statuses are updated and the stop conditions are checked 620. By sending the sort commands 634 and receiving a sort verification signal 636, the sorting software 604 creates a sort feedback loop. The sort feedback loop may be used to ensure that the exact sort limits are reached and that the sorting software 604 knows exactly which particles have been sorted to which output streams. If after the stop conditions are checked and the sort statuses are updated (step 620), it is found that all the stop conditions are met and the particles are verified as sorted, the sort is stopped 638. At step 638 the system might also enable index sorting and optimal sort rates. With the updated sort statistics 620, the final sort result is stored in the event frame 622. The final sort events and statuses 644 are stored in the event and status storage area on the computer at step 640. The sort decisions and verification statuses 644 are available to end user clients 642 for analysis and reporting on sort operations. Multiple end user clients 642 may access the system concurrently using a network connection. The network connection may be an Internet connection and the multiple end user clients 642 may be accessing the system using a web browser.

Figure 7:
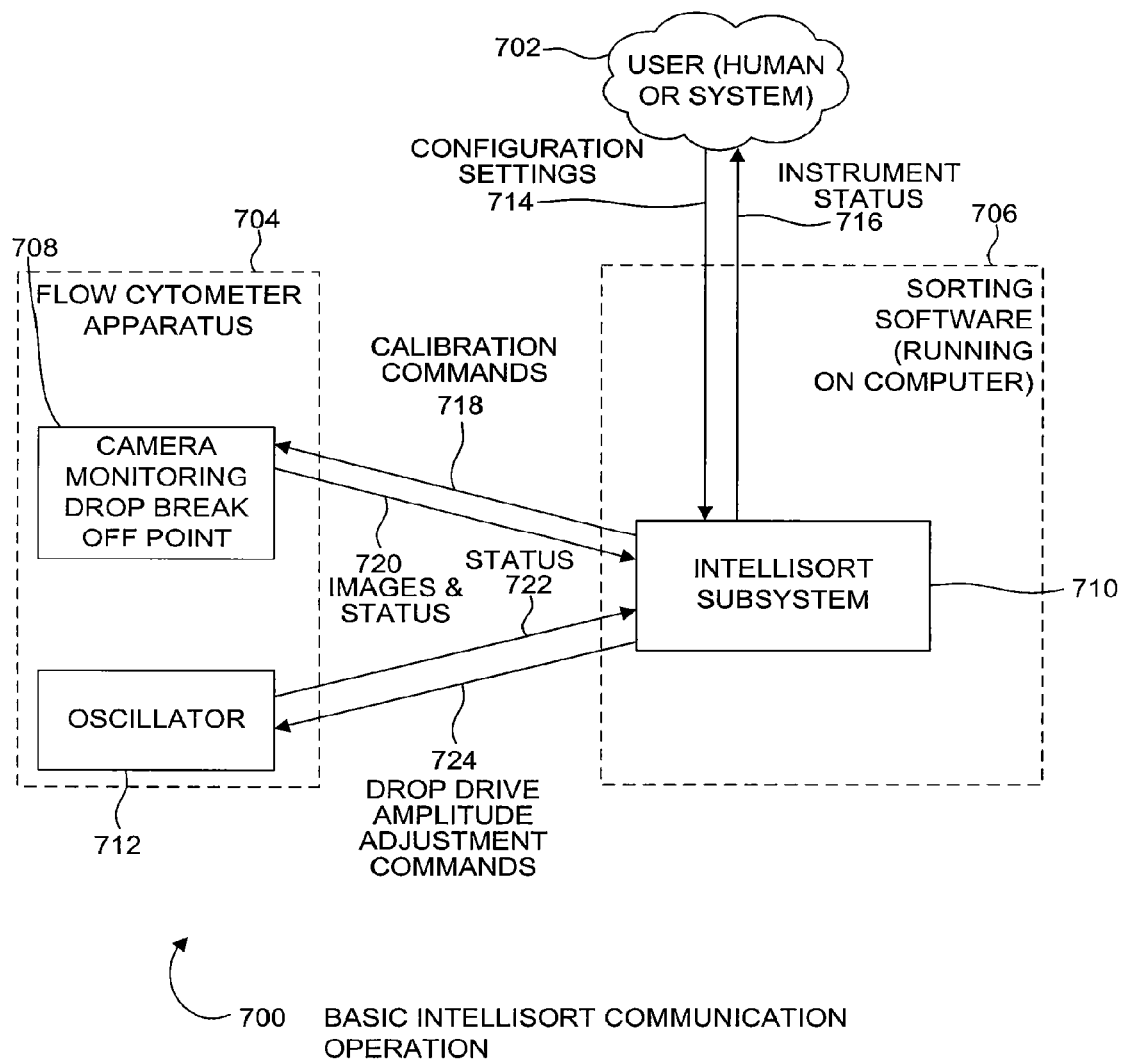
FIG. 7 is a schematic illustration of the basic communication operation for the Intellisort feature within the sorting software in one embodiment.

FIG. 7 is a schematic illustration 700 of the basic communication operation for the Intellisort 710 feature within the sorting software 706. Intellisort 710 is a feature that automatically adjusts the system to permit the flow cytometer apparatus 704 to have a more stable drop and to maintain a stable drop delay. Intellisort 710 uses a camera 708 to monitor the drop break off point of the stream in the flow cytometer apparatus 704 and compare the current image profile of the break off point to an initial image profile recorded at the time the drop delay was initially calculated. If the current image profile of the break off point differs from the image profile at the time the drop delay was initially calculated, the flow cytometer apparatus 704 is sent commands to adjust the drop drive amplitude 724 of the oscillator 712 such that the current image profile of the stream tends to return to the initial image profile when the drop delay was measured (i.e., the initial image profile). The oscillator 712 is the subsystem of the flow cytometer 704 that creates the vibrations in the stream which, in turn, cause the stream to break off into drops. One of the most important areas of the stream image profile to compare is the neck area of the stream where the stream narrows as the drop is ready to break off from the stream. By keeping the image profile constant the drop break off is more stable and the drop delay is more consistent and stable. A stable drop and drop delay benefits the system by reducing errors caused by slight variations in drops and in the drop delay that may be caused by minor fluctuations in outside factors such as air pressure, humidity, ambient temperature, fluid temperature, instrument temperature, etc.

The basic Intellisort communication operation 700 shown in FIG. 7 pertains primarily to the exchange of data between the flow cytometer apparatus 704 and the Intellisort subsystem 710 of the sorting software 706. A user 702, either human or automated, sends instrument configuration settings 714 to the Intellisort subsystem 710 of the sorting software 706. The Intellisort subsystem 710 converts the instrument configuration settings 714 into instrument calibration commands 718 that are sent to the camera monitoring the drop break off point of the stream 708. The camera sends a continuous image stream 720 to the Intellisort subsystem 710. The camera also sends instrument status messages 720 to the Intellisort subsystem as needed. The configuration settings 714 may also include setting the initial drop delay. The Intellisort subsystem 710 records the initial image profile of as the image being received 720 at the time the drop delay is set. An image profile is not a single image, but a group of images that record how a drop breaks off from the stream. The formation of the drop causes a narrow neck above the drop prior to the drop breaking off. The neck above the drop is one of the most important aspects to monitor when comparing image profiles. The Intellisort subsystem 710 continues to receive images 720 from the camera 708 as the flow cytometer apparatus functions. The Intellisort subsystem 710 compares the current image profile against the initial image profile. If the initial and current image profiles differ, the Intellisort subsystem calculates an adjustment to the oscillator amplitude that will cause the stream break off point current image profile to match the initial image profile. The adjustment to the oscillator amplitude is sent to the oscillator 712 as drop drive amplitude adjustment commands 724. The oscillator 712 sends the Intellisort subsystem 710 instrument status messages 722 to indicate the current status of the oscillator 712. The camera and oscillator status reported to the user 702 via instrument status message 716 sent by the Intellisort subsystem 710.

Figure 8:
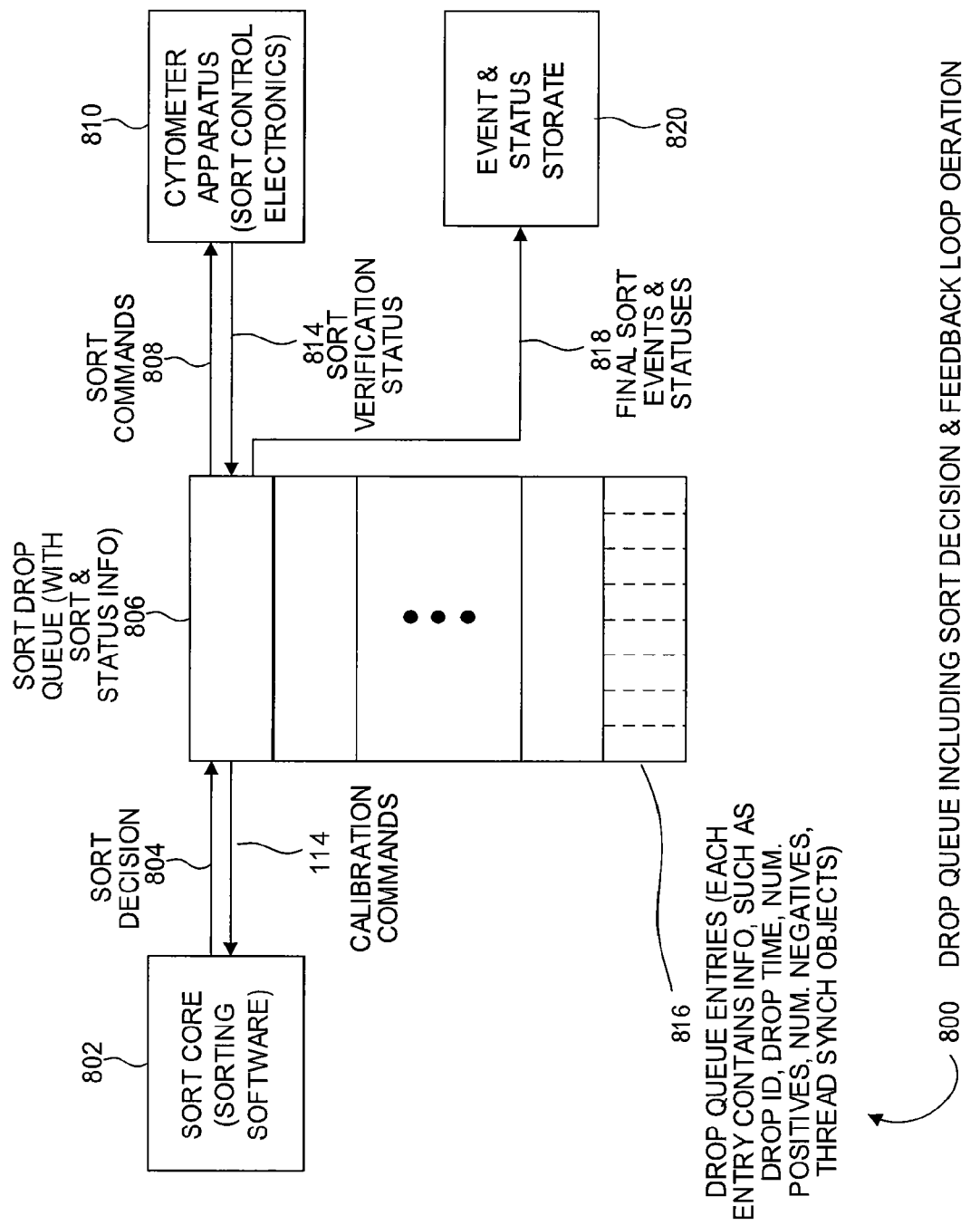
FIG. 8 is a block diagram of drop queue operation for sort decision and feedback loop operation in one embodiment.

FIG. 8 is a block diagram 800 of drop queue operation for sort decision and feedback loop operation. The sort core of the sorting software 802 calculates a sort decision 804 and sends the sort decision 804 to the drop queue 806. The drop queue contains entries for each drop 816. Each drop entry 816 may contain a variety of information such as a drop ID (identification), the drop time, number of positive particles for the drop, the number of negative particles (contaminants) for the drop, and thread synching objects for use by the thread safe implementation features of the sorting software. The drop time is measured using the same scale used to measure the time of particles detected by the flow cytometer acquisition electronics. Thus, the drop time may be measured using the ADC time or the drop time may be measured using the drop index which measures time in number of drops. The drop queue 806 passes the sort decision 804 to the cytometer sort control electronics 810 as sort commands 808 formatted for the cytometer apparatus sort control electronics 810. The cytometer sort control electronics 810 attempts to sort the drops based on the sort commands 808. The cytometer sort control electronics 810 returns the sort verification status 814 for each drop back to the drop queue 806. The sort verification status 814 contains information on whether a drop was sorted and which output stream where a sorted drop was sent. The drop queue 806 sends the sort verification status 812 back to the sort core of the sorting software 802 to complete the verification feedback loop. The drop queue also send the final sort event and status information 818 to the event and status storage 820 where the information may be accessed by users to report on and analyze sort operations.

Figure 9:
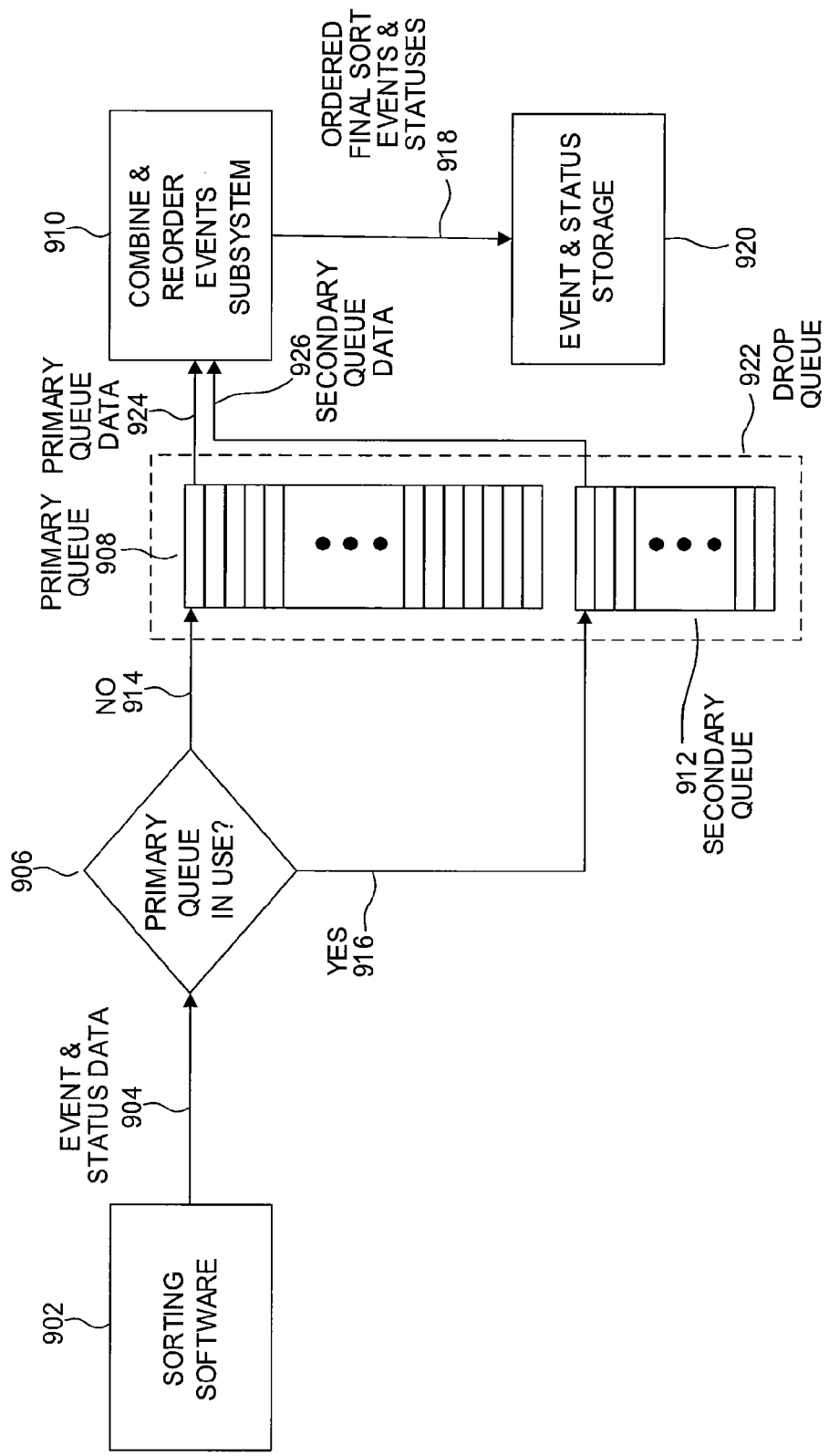
FIG. 9 is a block diagram of the operation of a non-blocking, thread-safe drop queue in one embodiment.

FIG. 9 is a block diagram 900 of the operation of a non-blocking, thread-safe drop queue 922. For threading applications, a thread using a segment of memory, such as that used for a queue, blocks access to the memory until the thread has completed operations on the segment of memory. Thus, while one thread is using the segment of memory other threads are blocked from accessing the segment of memory. For a time sensitive application having access to the memory segment blocked may not be acceptable and a command and control thread may need to always be able to access a segment of memory regardless of whether another thread is accessing the segment of memory. The sorting software 902 needs to be able to quickly write event and status data 904 to the drop queue 922 whether or not the drop queue is currently blocked by another thread. For the situation shown in FIG. 9, the sorting software 902 sends event and status data 904 to the drop queue 922.

The drop queue may be made up of two separate queues, a primary queue 908 and a secondary queue 912. The primary queue 908 may be accessed by threads other than the sorting software thread while blocking the sorting software thread from accessing the primary queue 908. The secondary queue 912 is exclusively for use by the sorting software thread 902. Prior to writing the event and status data 904 into the drop queue 922, it is determined whether the primary queue is in use at diagram block 906. If the primary queue 908 is not in use, the event and status data 904 is written into the primary queue 908. If the primary queue is in use 916, the event and status data is written to the secondary queue 912. Thus, the sorting software 902 is able to quickly write data to the drop queue 922 even when another thread is blocking access to the primary queue 908. When the overall system operation has available computing time and access to the primary queue 908 is no longer blocked, the primary queue data 924 and the secondary queue data 926 is combined and reordered by the combine and reorder events subsystem 910. The combine and reorder events subsystem 910 takes the secondary queue data 926 and merges it into the primary queue 908 during a read operation. The combine and reorder events subsystem 910 may also reorder the drop queue 922 entries so that the secondary queue data 926 is placed at the proper chronological location in the primary queue 908. During the read operation, the ordered final events and statuses 918 are then sent to and stored in the event status storage area 920. The actions described to make the drop queue non-blocking and thread-safe may also be employed to make the event queue non-blocking and thread-safe.

Figure 10:
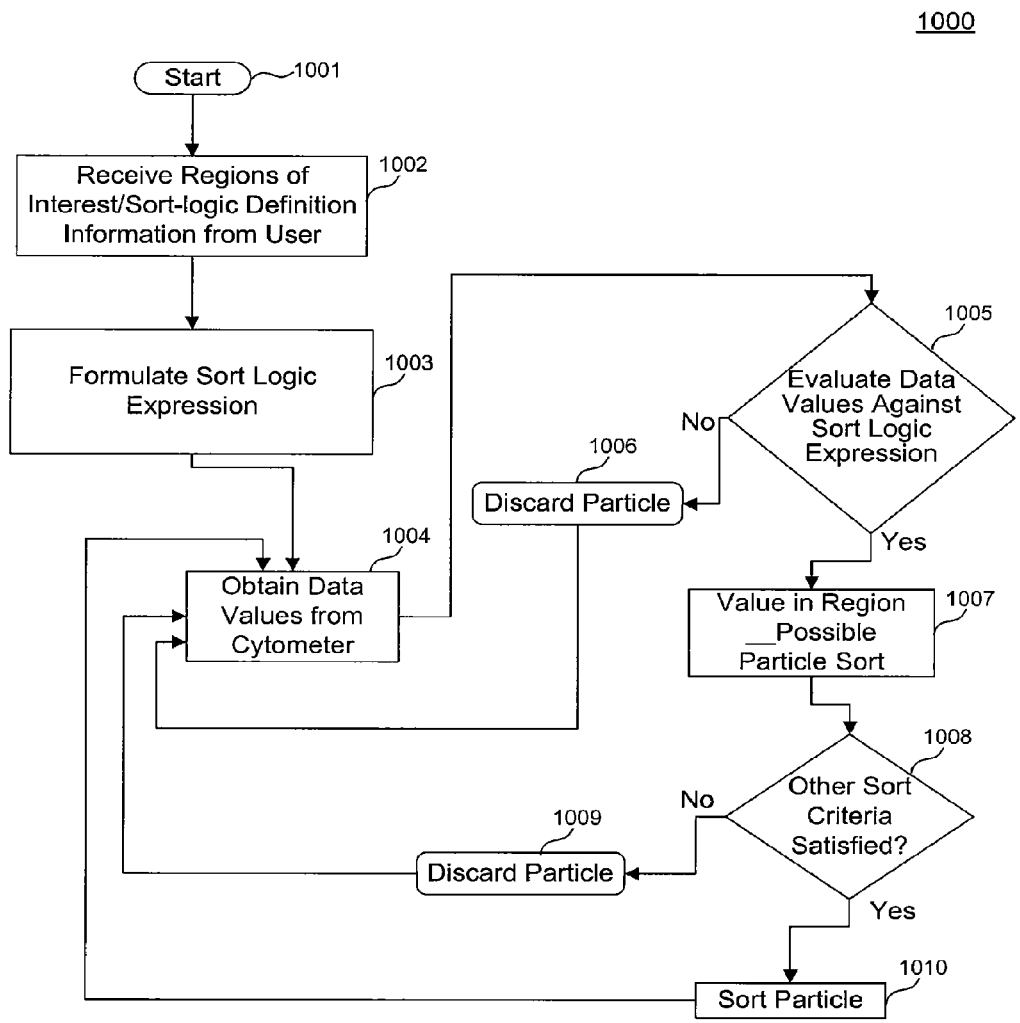
FIG. 10 is a flow chart of an example method of using received sort logic definition in the sorting of particles in one embodiment.

Referring back to FIG. 2, additional detail of an exemplary processing in step 210 is illustrated in FIG. 10. Steps 1002 and 1003 may typically be carried out each time the user input provided in step 204 includes modifications to the regions of interest selected for sorting. Steps 1004-1010 illustrate an exemplary processing path repeated in software for each particle that is detected in the flow cytometer apparatus 104 and for which data is received by the software sorting module 106.

The sort logic definition provided by the user in step 204 and received by the sorting software in step 1002 may include sets of parameters that delineate regions of interest that correspond to many mathematically definable geometric shapes. The parameters received in the sort logic definition may be used in formulating mathematical equations that represents the one or more regions of interest indicated by the user. As described below, each of the user specified regions of interest may be formulated as a mathematical equation that evaluates to less than zero if the relevant particle data is within that region of interest. In step 1003, the parameters received from the user may be incorporated to a sort logic expression that may comprise a Boolean combination of mathematical equations defining the user indicated regions of interest. In some embodiments, the received sort logic definition may provide all or part of the sort logic expression. The sort logic expression constructed in step 1003, may then be used in step 1005 to determine if the particle to be sorted belongs to a given region of interest. If the particle data is determined to be within the subject region of interest in step 1005, then in step 1006 the particle is identified for further evaluation and proceeds to step 1008. Additional sort criteria, including additional regions of interest, may be considered in step 1007 before the sort or no-sort decision is made in 1010.

In embodiments of the present invention, the user may define a region of interest by, for example, drawing on a computer screen with one or more input devices. In some embodiments of the present invention, data generated from an initial run of sample data is displayed to the user so that the user may indicate the regions of interest having data points that correspond to particles that the user wishes to sort. The definition of the regions of interest included in the user logic definition, may be generated by the user using a combination of methods including, but not limited to, marking on the display screen boundaries around regions of interest, providing numeric measures indicating ranges of desired values in selected dimensions and confirming regions of interest determined by the system. The dimensions considered may correspond to measured quantities such as, but not limited to, forward scatter, side scatter and fluorescence in a range of spectra.

By way of example, the user may observe in the sample data displayed in the form of an X-Y plot (i.e., plots mapping X and Y as dimensions to be considered) on a screen regions of interest that can be delineated in many mathematical forms, for example: a region of interest between two lines parallel to the Y-axis; a region of interest between two lines not parallel to either axis but which can be represented, as is well known, by equations of the form Y=mX+c, where m corresponds to the slope of the curve and c corresponds to the point at which the y-axis is intercepted; rectangular areas that are definable by specifying upper and lower bound values to each measured dimension or by more generally specifying equations that correspond to the upper and lower bounds; and regions of interest that can be delineated with other simple curves including various conic sections including, but not limited to, circular regions, elliptic regions, and parabolic regions. In general, in the two dimensional system, a plurality of conic sections can be defined by an equation of the form $P_q=Ax^2+Bxy+Cy^2+Dx+Ey+F=0$, where the constants A, B, C, D, E and F are parameters defined for each particular instance and where A, B, and C are not all zero. For example, if A=C and B=0, then $P_q$ represents a circle. If $B^2-4AC<0$, $P_q$ represents an ellipse. If $B^2-4AC=0$, $P_q$ represents a parabola. If $B^2-4AC>0$, $P_q$ represents a hyperbola. Based on user input, the constants A, B, C, D, E, and F may be derived. During the sort operation in step 1005, for purposes of illustration only and without limitation, the equation $P_q$ is evaluated using the predetermined constants A-F and the actual measured values of x and y. When evaluated, values less than zero, in general, would indicate that the particle from which the data point was obtained lies within the region of interest defined by $P_q$ and therefore should be selected as a candidate for sorting.

The methods described herein to define regions of interest need not be limited to polynomial expressions of second order or to expressions defined in only two dimensions. For instance, a general polynomial expression of order n, P2, $$n = \sum_{k=0}^{n} \sum_{i=0}^{k} a_{k,i} x^{k-i} y^i = 0$$

may be formulated in order to characterize regions of interest bounded by complex shapes, such as those having multiple lobes, embayments, or other concave or convex curves, in a two dimensional Cartesian plane. As another example, in three dimensions (coordinate axes x, y and z), a general polynomial expression of the second order may be formulated as $P_{3,2}=k_{11}x^2+k_{12}xy+k_{13}xz+k_{22}y^2+k_{23}yz+k_{33}z^2+k_1x+k_2y+k_3z+k_4=0$ in which $k_{11}$, $k_{12}$, $k_{13}$, $k_{22}$, $k_{23}$, $k_{33}$, $k_1$, $k_2$, $k_3$, and $k_4$ are parameters which are used to define various boundary surfaces of volumetric regions of interest and which are provided, either directly or indirectly by the user. A user may also specify an enclosing surface in three or more dimensions using other means such as computer graphics rendering techniques that can display multiple virtual surfaces and allow the user to select, for example by pointing with a computer mouse, the boundary surfaces defining a region of interest. Alternatively, software may determine a set of multidimensional regions of interest and present that set to the user for modification and selection. For example, software may determine surfaces bounding a region of interest in several dimensions and prompt the user for one or more dimensions, or the software may determine all of the relevant surfaces bounding the region of interest.

Various embodiments permit a flow cytometer to perform expanded sort logic beyond a two-dimensional oscilloscope like selection. Three or more dimensional regions may be selected for sorting. Thus, a sample may be filtered to more precisely meet a user's desired output stream. Sort decisions may include all Boolean logic functions such as AND, OR, and NOT gates. Further, complex user-defined mathematical equations may be incorporated into the sort decision, including calculations based on the results of other calculations and not solely based on raw data values sensed by the flow cytometer apparatus. Wider sort envelopes permit higher quality output streams by eliminating possible contaminants. Overlapping sort decisions may be enhanced by tracking which stream received a drop in the case where one or more output streams were selected to receive the drop. Overall, various embodiments permit a highly robust and configurable system. System speed and precision may be increased by preprocessing the data delivered by the flow cytometer apparatus. Drop and drop delay stability may be increased by using a camera to observe the stream break off point and adjust the system to maintain the image profile of the stream break off point recorded when the drop delay was measured. Events and verification statuses may be recorded for use by multiple end user clients in reporting and analyzing sort operations.

The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A system for sorting particles from a particle stream, comprising:
   (a) a flow cytometer; and
   (b) a computer coupled to the flow cytometer, wherein the computer comprises:
      (i) an input device that receives a sort logic definition;
      (ii) a sort parameters module that calculates while a particle is passing through the flow cytometer one or more sort decision making parameters based on raw event data values for the particle passing through the flow cytometer received from the flow cytometer and the sort logic definition; and
      (iii) a sort decision module wherein the sort decision module determines one or more sort decisions by performing sort logic computations while the particle is passing through the flow cytometer using the sort logic definition and the one or more sort decision making parameters, and wherein the sort decision module converts the one or more sort decisions into one or more sort commands to control the sorting of the particle and sends the one or more sort commands to the flow cytometer.

2. The system of claim 1, wherein the computer further comprises an event status and storage module and wherein the event status and storage module stores the one or more sort decisions and corresponding sort status and verification data.

3. The system of claim 1, wherein the sort decision module performs sort logic computations algorithmically using conditional branching logic.

4. The system of claim 3, wherein the conditional branching logic includes sort logic equations included in the sort logic definition.

5. The system of claim 1, wherein performing sort logic computations further includes using one or more sort logic equations in software on the computer, and wherein said sort logic equations include one or more mathematical functions characterizing one or more regions of interest in multidimensional space.

6. The system of claim 5, wherein said one or more mathematical functions are determined based on one or more parameters provided by a user.

7. The system of claim 2, wherein the storage module stores the sort status and verification data with the one or more sort commands and the raw event data values for a particle.

8. The system of claim 7, further comprising:
   an output device providing user access to at least one of the one or more stored sort verification status values, the one or more sort commands, and the one or more raw event data values for a particle.

9. The system of claim 1, wherein the computer is an embedded computer in the flow cytometer.

10. The system of claim 1, wherein the computer is a server in network communication with the flow cytometer.

11. The system of claim 1, wherein the raw event data values are represented by at least sixteen bits.

12. The system of claim 1, wherein the raw event data values are represented by at least 32 bits.

13. The system of claim 1, further comprising:
   an output device reporting to a user information in a multidimensional data space based on measurements of a sample obtained using a flow cytometer, and wherein the input device, responsive to receipt of the information by the user, receives information indicating the user's selection of the one or more regions of interest in multidimensional data space.

14. The system of claim 13, wherein in the output device includes a graphical interface displaying information in a multidimensional data space based on measurements of a sample obtained using the flow cytometer.

15. The system of claim 14, wherein the input device receives inputs identifying regions of interest in the multidimensional data space based on user drawn boundaries on a computer screen around the regions of interest.

16. The system of claim 14, wherein the input device receives inputs identifying regions of interest in the multidimensional data space based on user identification of particles that the user wishes to sort in the regions of interest.

17. The system of claim 14, wherein the input device receives inputs identifying regions of interest from the user based on the user indicating ranges of desired values in selected dimensions for the regions of interest.

18. The system of claim 14, wherein the input device receives inputs from the user indicating the user's confirmation that the regions of interest determined by the system are the regions desired by the user.

* * * * *